United States Patent
Nakagaki et al.

(10) Patent No.: US 7,034,299 B2
(45) Date of Patent: Apr. 25, 2006

(54) TRANSMISSION ELECTRON MICROSCOPE SYSTEM AND METHOD OF INSPECTING A SPECIMEN USING THE SAME

(75) Inventors: Ryo Nakagaki, Kawasaki (JP); Yuji Takagi, Kamakura (JP); Hirohito Okuda, Yokohama (JP); Hiroshi Kakibayashi, Nagareyama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 32 days.

(21) Appl. No.: 10/918,340

(22) Filed: Aug. 16, 2004

(65) Prior Publication Data

US 2005/0051725 A1    Mar. 10, 2005

(30) Foreign Application Priority Data

Sep. 8, 2003  (JP)  ............................. 2003-314909

(51) Int. Cl.
*H01J 37/26* (2006.01)
*G01N 23/04* (2006.01)

(52) U.S. Cl. ...................... 250/311; 250/307; 250/304; 382/128

(58) Field of Classification Search ...................... None
See application file for complete search history.

(56) References Cited

U.S. PATENT DOCUMENTS 6,875,984 B1 * 4/2005 Kakibayashi et al. ........ 250/311
2004/0120557 A1 * 6/2004 Sabol et al. ................. 382/128

* cited by examiner

*Primary Examiner*—Jack I. Berman
(74) *Attorney, Agent, or Firm*—Antonelli, Terry, Stout and Kraus, LLP.

(57) ABSTRACT

It is possible to reliably and efficiently determine whether a specimen contains viruses, bacteria, etc. and, if it does, identify their types, regardless of the observer. Furthermore, even a newly-discovered bacterium can be quickly identified by utilizing a database at a remote location. A transmission microscope system has a microscope for observing a specimen and a database which stores, for each microscopic thing (such as a virus), a name, a specimen pretreatment method and an imaging condition used when the microscopic thing is observed, captured image data, etc. An image of the specimen is captured according to a specimen pretreatment method and an imaging condition retrieved from the database using the name of a target microscopic thing as a key, and the captured image is compared with images stored in the database to identify microscopic things present in the specimen.

19 Claims, 7 Drawing Sheets

| NAME | IMAGE DATA | IMAGING CONDITIONS | PRETREAT-MENT | SYMPTOMS | FEATURES |
|---|---|---|---|---|---|
| VIRUS A | | ACCELERATION VOLTAGE:50kV MAGNIFICATION: | STEP1: ··· STEP2: ··· STEP3: ··· | FEVER | SPHERICAL: ABOUT 20 NM IN DIAMETER |
| VIRUS B | | ACCELERATION VOLTAGE:40kV MAGNIFICATION: | STEP1: ··· STEP2: ··· STEP3: ··· | VOMITING DIARRHEA | ELLIPSOIDAL SPECKLED |
| ⋮ | ⋮ | ⋮ | ⋮ | ⋮ | ⋮ |

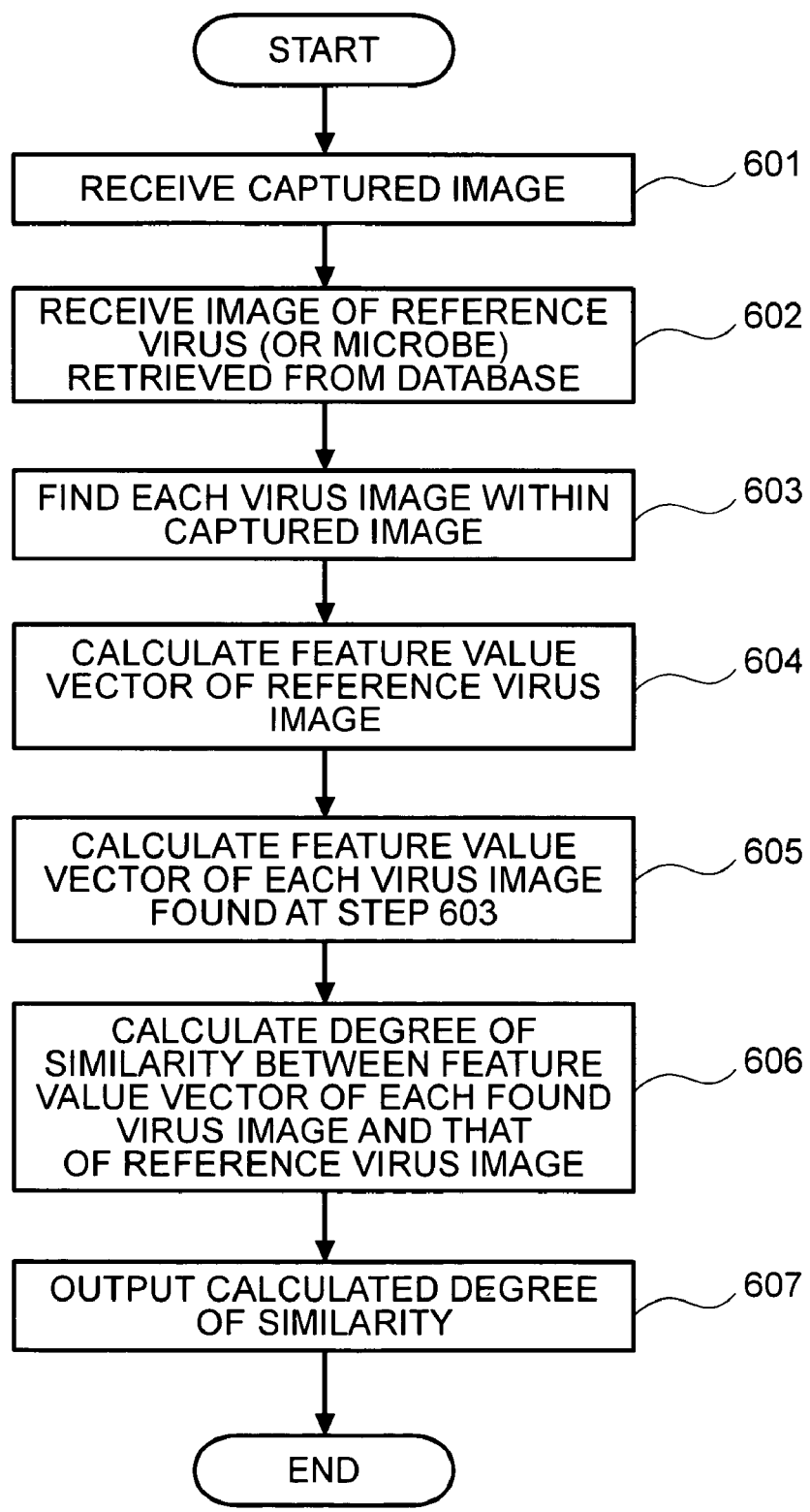

TRANSMISSION ELECTRON MICROSCOPE SYSTEM AND METHOD OF INSPECTING A SPECIMEN USING THE SAME

BACKGROUND OF THE INVENTION

The present invention relates to a transmission electron microscope system for observing an obtained specimen under a microscope to determine whether it contains microorganisms and, if it does, to identify their types in order to identify the cause of a disease or carry out food sanitation supervision. The present invention also relates to an inspection method using this transmission electron microscope system.

When dealing with a disease or a food poisoning case caused by a virus or bacterium, the first thing to do is to identify the cause of the symptoms that the people or livestock are suffering. In such a case, a sample of fecal matter, etc. is gathered from a patient, etc., and this sample is checked to see if it contains any virus or bacterium. Since viruses and bacteria are very small, observing them usually requires a microscope which allows observation of minute samples at high resolution, such as a transmission electron microscope. Since transmission electron microscopes form an image using electrons transmitted through the sample, they are also suitable for observing substances having a minute three-dimensional structure, such as protein.

For example, the H-7600 transmission electron microscope catalog from Hitachi High-Technologies Corporation lists transmission electron microscopes for such a purpose. A transmission electron microscope is made up of an electron gun, an irradiation system electron lens, a sample holder stage, an imaging system lens, a camera, a vacuum pumping system, a control system, etc.

When viruses in a specimen are observed using such a microscope, fecal matter or living tissue, for example, is gathered from a test subject and pretreated so that it can be actually observed under a transmission electron microscope as a specimen.

Samples for observation are broadly classified into three types: (1) negatively stained samples, (2) stained sliced samples, and (3) frozen sliced samples.

(1) A negatively stained sample is prepared by purifying and concentrating living tissue, fecal matter, etc. by use of a reagent or a centrifugal separator and then mounting it on a mesh for electron microscopes. Representative examples of negatively stained samples are fine granular specimens of viruses, etc. Tungstic acid is usually used as the staining agent. When this type of sample contains viruses, a levee (or a low wall) is formed around each virus, providing contrast between each virus and its levee.

(2) A stained sliced sample is prepared by slicing living tissue of an animal or plant with a diamond cutter, etc. to produce a slice having a thickness of a few tens of nanometers and then mounting the slice on a mesh for electron microscopes. Before and when slicing the living tissue, it must be subjected to processes such as fixing, dehydrating, embedding, and cutting. Generally, the tissue must be stained so as to provide enough contrast to observe its structure under an electron microscope. Suitable staining agents include reagents containing a heavy metal, such as uranium acetate, lead citrate, lead hydroxide, and lead acetate. Usually, the tissue is double-stained with uranium and lead. Staining is required since a living body is primarily made up of light elements, such as hydrogen, oxygen, carbon, and nitrogen. That is, these elements only exhibit a small scattering power with respect to electron beams and, furthermore, they differ only a little in such power, resulting in very low image contrast. What is stained in the tissue is its protein; the higher the protein concentration, the more heavily the tissue is stained. As a result, the obtained electron microscope image has a contrast according to the protein concentration.

(3) A frozen sliced sample is prepared by bring living tissue into contact with a copper block, which has been cooled down by liquid helium or liquid nitrogen so as to freeze the tissue and then slicing the frozen tissue by use of a cooling stage and a microtome. This type of sample was devised to observe a tissue structure in an active state. Therefore, the tissue is neither fixed nor stained, and it is observed under a cryo-electron microscope equipped with a cooling sample stage. Since the sample tissue is not stained, the contrast of the obtained image is low.

A sample pretreated as described above for observation is mounted on the stage of an electron microscope and observed by magnifying its image a few tens of thousands to a few hundreds of thousands of times. When identifying microorganisms, such as viruses contained in the sample, a person observes the magnified image to determine whether it includes virus images based on the characteristic shape and internal structure of each virus, and, if the image contains any virus image, to identify the type of virus. Further, when analyzing the structure of a protein(s) in the sample, several magnified images are taken of the sample to be observed while the sample stage of the electron microscope is being tilted. The taken images are subjected to CT (computer tomography) processing to provide a fine three-dimensional structure having dimensions on the order of a few tens of nanometers.

Recently, a transmission electron microscope has been provided with (or to include) a control personal computer having autofocus and imaging (control) capabilities to increase the efficiency of the observation work. However, the user must still determine whether a sample contains microorganisms, such as viruses, and to identify their types based on captured images. Actually, the user compares each possible virus image against images of previously found viruses listed in books and other documents to identify each imaged microorganism (virus).

A problem with such a method is that it takes considerable time to identify each virus. This is because the captured image includes images of various things other than microorganisms to be identified, making it necessary to discriminate each target microorganism from them. Furthermore, manually searching a huge amount of past microorganism data requires substantial time and labor. Further, there is another problem in that virus identification may or may not be accurate depending on the skill of the observer or the degree of fatigue suffered by the observer.

Further, still another problem arises when it is necessary to handle a new virus, etc. That is, viruses and microbes grow and mutate into new forms, meaning that a new (undiscovered) virus may suddenly appear. As a result, the documents at hand might not list a virus currently under observation, which may make it necessary to consume a large amount of time to identify the virus.

A similar problem arises, for example, when it is necessary to determine whether a case of a disease found in Japan has been caused by a microorganism which usually exists locally in some other part of the world, such as Africa. When this occurs, a sample is usually sent to large research institutes in the world to identify the microorganism which has caused the case. This may lead to a delay in identifying and handling the microorganism.

SUMMARY OF THE INVENTION

The present invention provides a transmission electron microscope system that is capable of easily determining whether a specimen contains microorganisms and, if it does, identifying their types, thereby solving the above-described art problems. The present invention also provides an inspection method using such a transmission electron microscope system.

Further, the present invention also provides a network system capable of quickly determining whether a virus in a specimen is identical to a virus newly discovered at a remote location by gathering information on the new virus through a wide area network.

A transmission electron microscope system of the present invention comprises: means for accessing a database which stores transmitted electron images of different types of microorganisms and specimen pretreatment methods and imaging conditions for capturing the transmitted electron images; an input unit for inputting a keyword for selecting a microscopic thing whose presence or absence in a specimen is to be determined; means for receiving a transmitted electron image of the microscopic thing and a specimen pretreatment method and an imaging condition selected based on the input keyword; an imaging unit for capturing an image of the specimen under the received imaging condition after the specimen is pretreated by the received pretreatment method; a comparison unit for comparing the image captured by the imaging unit with the image received from the database; and an output unit for outputting a comparison result received from the comparison unit.

Further, the present invention also provides a network system in which the above-mentioned transmission electron microscope system and one or more database creation sites are connected to a wide area network. This system is characterized in that the transmission electron microscope system accesses a database created from all or some of the original databases stored in the above-mentioned database creation sites.

The transmission electron microscope system of the present invention makes it easy to determine whether a specimen contains microorganisms and, if it does, to identify their types. Furthermore, it is possible to quickly determine whether a virus in a specimen is identical to a virus newly discovered at a remote location by gathering information on the new virus through a wide area network.

These and other objects, features, and advantages of the invention will be apparent from the following more particular description of preferred embodiments of the invention, as illustrated in the accompanying drawings.

BRIEF DESCRIPTION OF THE DRAWINGS

FIG. 6 is a flowchart showing determination processing in the microscope system for calculating a degree of similarity;

DESCRIPTION OF THE PREFERRED EMBODIMENTS

Preferred embodiments of the present invention will be described below.

Figure 1:
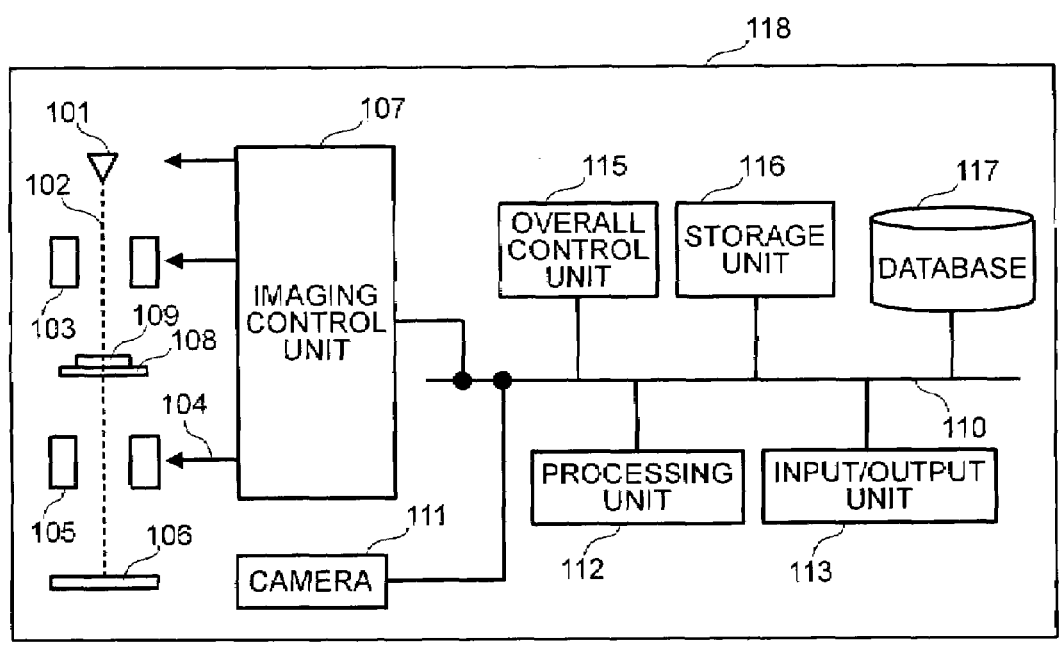
FIG. 1 is a block diagram showing the configuration of a microscope system according to the present invention.

FIG. 1 shows a transmission electron microscope system 118 according to the present invention. The system 118 comprises: an imaging system; an input/output unit 113 for inputting and outputting data; a processing unit 112 for processing image data; a storage unit 116 for storing processing results, etc.; a database 117 for providing reference data used to identify an imaged microscopic thing; an overall control unit 115 for controlling the operation of each unit; and an internal bus 110 for interconnecting each unit. The imaging system includes an electron gun 101, an irradiation lens 103, an objective lens 104, an imaging lens 105, a fluorescent screen 106, an imaging control unit 107, a mesh 108 on which a specimen 109 to be observed is mounted, and a camera 111.

The present system (118) captures an image in the same manner as an ordinary transmission electron microscope. Specifically, the process begins by obtaining human excrement or cellular structure considered to contain microorganisms, etc. to be observed. Then, a predetermined pretreatment is applied to the obtained sample to produce a specimen observable with a transmission electron microscope, which specimen is then mounted on the mesh 108. The above-mentioned pretreatment is needed to change the obtained sample into a specimen suitable for observation under a microscope, since the sample (human excrement or cellular structure) contains various things other than those to be observed. The above-mentioned pretreatment may include chemical treatment, centrifugal separation, and staining.

Then, imaging conditions, such as the acceleration voltage of an electron beam 102 and the observation magnification, are set appropriately for observation of the specimen. Such condition data may be entered by the operator through the input/output unit 113 using a keyboard or mouse, or it may be selected from the information stored in the storage unit 116 beforehand. The imaging condition data is fed to the imaging control unit 107 through the overall control unit 115. When an image is captured, the electron beam 102 emitted from the electron gun 101 is directed by the irradiation lens 103 and a deflector (not shown) such that it enters into the specimen at a right angle with respect to the surface of the specimen.

The electron beam transmitted through the specimen goes through the imaging lens 105, etc. and then forms an image on the fluorescent screen 106. At that time, the imaging control unit 107 controls the imaging lens 105 by use of a control signal 104 such that the image is captured at a predetermined magnification. The formed image is captured by the camera 111, and the captured image data is sent to the storage unit 116 through the internal bus 110.

In some cases, the image data is output to the input/output unit 113. Therefore, the input/output unit 113 includes a display monitor and a printer. The transmission electron microscope system of the present invention is configured so as to identify viruses, bacteria, etc. (hereinafter referred to as "microorganisms, etc.") based on image data obtained through the above-mentioned process. This process of identifying microorganisms, etc. will be described below.

Figure 2:
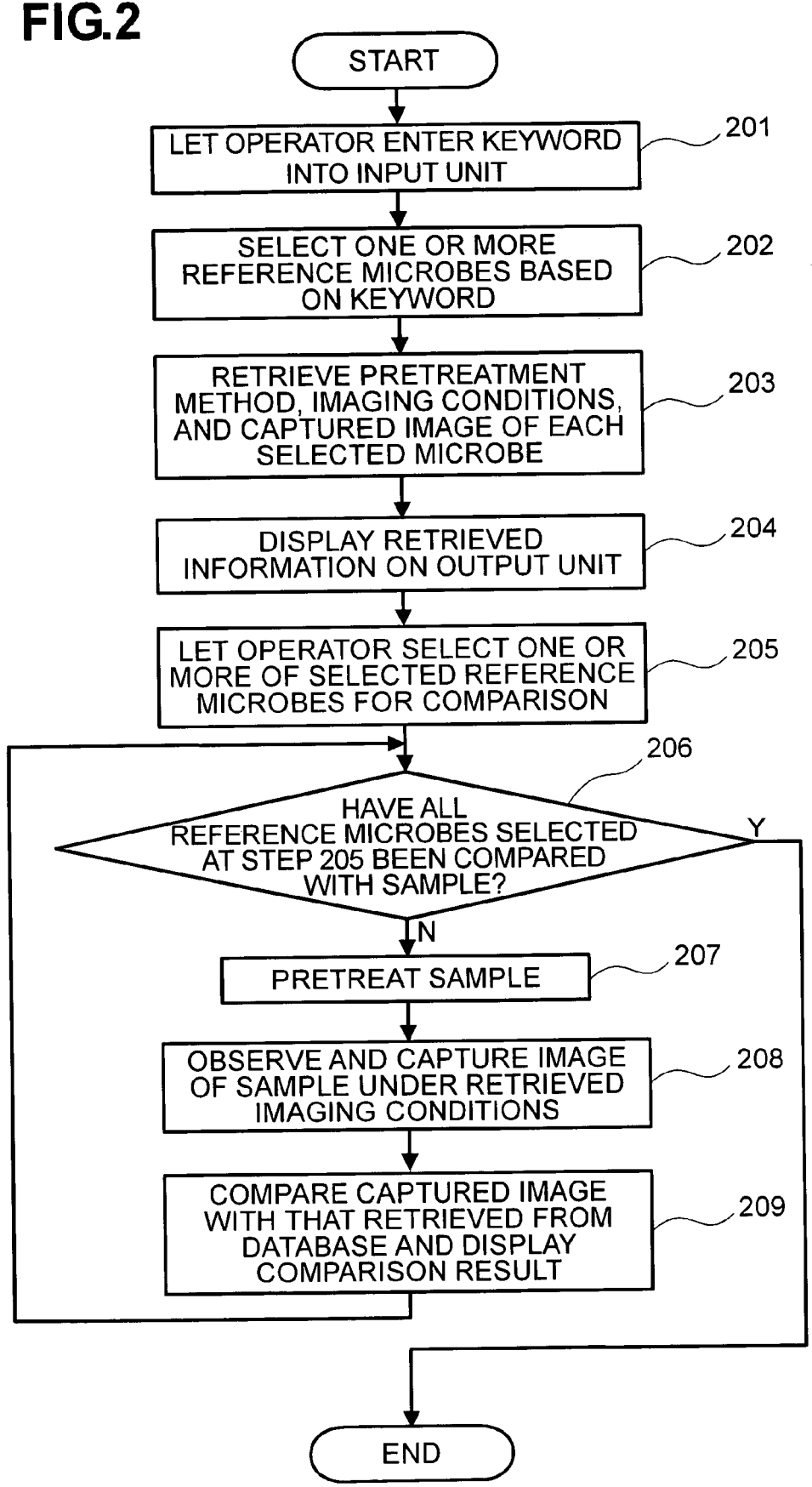
FIG. 2 is a flowchart showing a process of identifying microorganisms (microbes) according to the present invention.

FIG. 2 is a flowchart showing the process of identifying microorganisms (microbes), etc. Before initiating this process, the system operator prepares a sample of human excretion or blood. The purpose is to identify microorganisms, etc. contained in this sample. Then, the operator enters one or more keywords for selecting reference microorganisms (or candidate or target microorganisms), whose images are to be compared with an image of the sample, by use of the keyboard of the input/output unit 113 at step 201. These keywords may include any information for narrowing down the reference microorganisms. Examples of keywords include information indicating appearance characteristics of each target microorganism (such as spherical or ellipsoidal), or information on symptoms caused by the microorganism (such as stomachache, vomiting, or fever), or the specific name of a microorganism group to which the microorganism is considered to belong (such as "smallpox virus" or "influenza virus").

Then, at step 202, the overall control unit 115 selects one or more reference microorganisms whose images are to be compared with an image of the sample by searching the data on microorganisms, etc. stored in the database 117 using the received keywords.

Figures 3, 4:
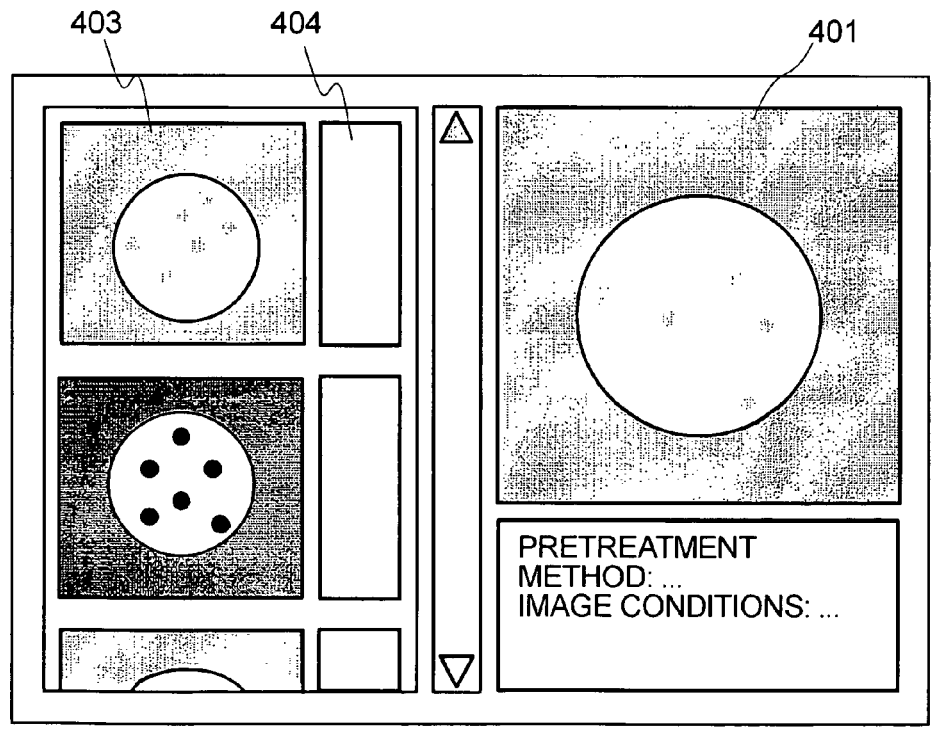
FIG. 3 is a table illustrating a microorganism database accessed by the microscope system.
FIG. 4 is a diagram showing an exemplary display screen of an input/output unit displaying database search results.

FIG. 3 shows an example of the configuration of the database 117 storing information on microorganisms, etc. Specifically, the database 117 stores various kinds of data on each microorganism in an organized manner. The database 117 may store any data indicating the characteristics of each microorganism, etc. For example, the stored data may include primarily, for each microorganism, the name, transmitted electron microscopic image data, the conditions under which the image was taken, the specimen pretreatment method used when the image was taken, information on symptoms caused by the microorganism, and information indicating the appearance and the size of the microorganism.

Such a database may be created by a research institute specializing in viruses or microbes. It should be noted that a plurality of pieces of image data may be obtained for the same microorganism. Especially, if a microorganism has a three-dimensional structure and therefore its appearance varies depending on the direction in which it is viewed, it is preferable to store a plurality of pieces of image data obtained as a result of imaging the microorganism in various directions.

As described above, at step 202, the overall control unit 115 selects from the database one or more reference microorganisms (whose images are to compared with an image of the sample) related to obtained keywords. For example, if the keyword "spherical" is given as appearance information, the overall control unit 115 checks the Features field of each microorganism in the database 117 and selects a plurality of microorganisms whose Features field is set to "spherical" as reference microorganisms. The overall control unit 115 also selects appropriate reference microorganism from the database 117 in the same manner if the given keyword is a symptom caused by a microorganism(s) or the name of a specific microorganism group (influenza, etc.)

At step 203, from the database 117, the overall control unit 115 reads out, for each selected microorganism, the specimen pretreatment method used when an image was taken, the conditions under which the image was taken, and the image data. The read data is stored in the storage unit 116 and displayed on the input/output unit 113 at step 204. This allows the operator to view the data on microorganisms, etc. stored in the database 117 and related to the keywords entered by the operator. If the retrieved data is not satisfactory, the operator may enter new keywords to repeat steps 201, 202, 203, and 204.

The operator may identify target microorganisms present in the sample based on the displayed image data at this point. However, to more accurately identify microorganisms in the sample, the following steps may be performed.

At step 205, through the input/output unit 113, first the operator selects one or more of the reference microorganisms selected from the database, for comparison with the sample. The overall control unit 115 receives the selection results and stores them in the storage unit 116.

Then, at step 207, the operator selects one of the reference microorganisms selected at step 205 and pretreats the sample using the sample pretreatment method for this reference microorganism read out from the database 117.

Then, the operator mounts the pretreated sample (specimen) on the mesh 108 and enters an instruction through the input/output unit 113 to initiate the imaging operation.

Upon receiving this instruction, the overall control unit 115 instructs the imaging control unit 107 to capture an image of the specimen under the imaging conditions for this reference microorganism stored in the storage unit 116. In response, the imaging system captures the image at step 208. After that, the image data obtained through the camera 111 is sent to and stored in the storage unit 116.

The image may be displayed on the input/output unit 113. When the captured image data has been stored in the storage unit 116, the overall control unit 115 sends the captured image stored in the storage unit 116 and the image data of the reference microorganism also stored in the storage unit 116 to the processing unit 112 and instructs the processing unit 112 to perform comparison and determination processing.

Alternatively, the operator may capture an image of the sample him or herself. In this case, the operator pretreats the sample by the sample pretreatment method (used when the image of the reference microorganism was taken) stored in the storage unit 116 and displayed on the input/output unit 113 at step 204 and then captures a transmitted electron image under the transmission electron microscope after the conditions of the microscope are set based on the displayed imaging conditions. The captured image is sent to and stored in the storage unit 116. The overall control unit 115 sends this captured image stored in the storage unit 116 and the image data of the current reference microorganism also stored in the storage unit 116 to the processing unit 112, which then performs comparison and determination processing.

FIG. 6 is a flowchart illustrating the comparison and determination processing in the processing unit 112 (for calculating a degree of similarity). The processing unit 112 receives the captured image data at step 601 and the image data of the reference microorganism at step 602 before initiating the processing. The captured image 501 shown in FIGS. 5A and 5B is a schematic representation of the above-mentioned captured image data, while the template image 506 is a schematic representation of the image data of the reference microorganism to be compared.

Figure 5A:
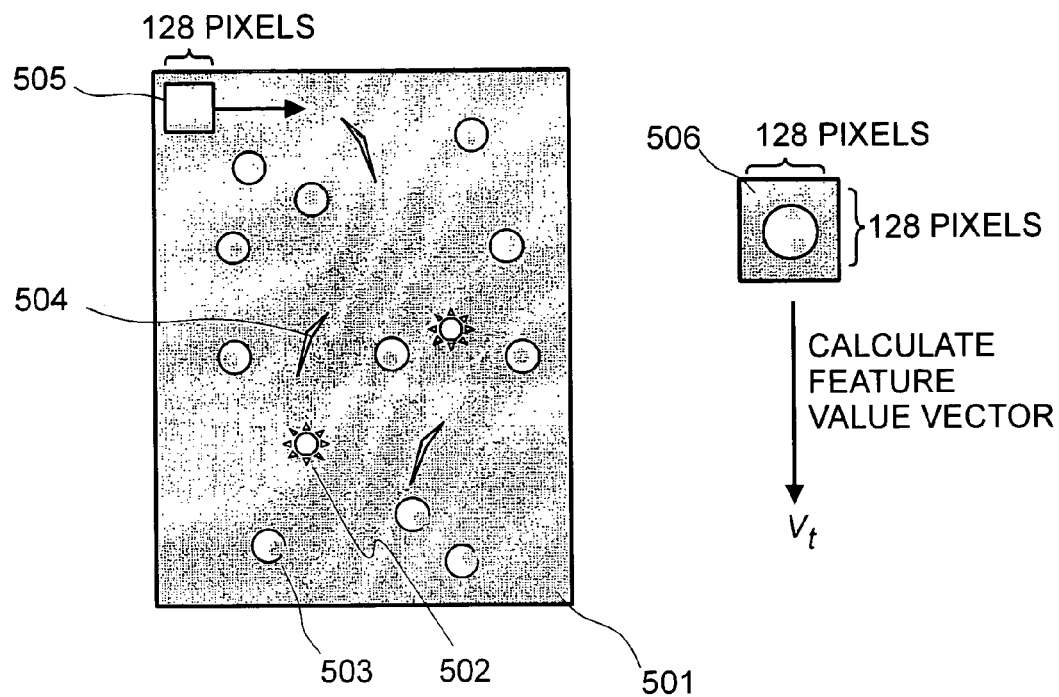
FIG. 5A is a diagram illustrating how a local window 505 is shifted by one pixel at a time within a captured image 501.
Figure 5B:
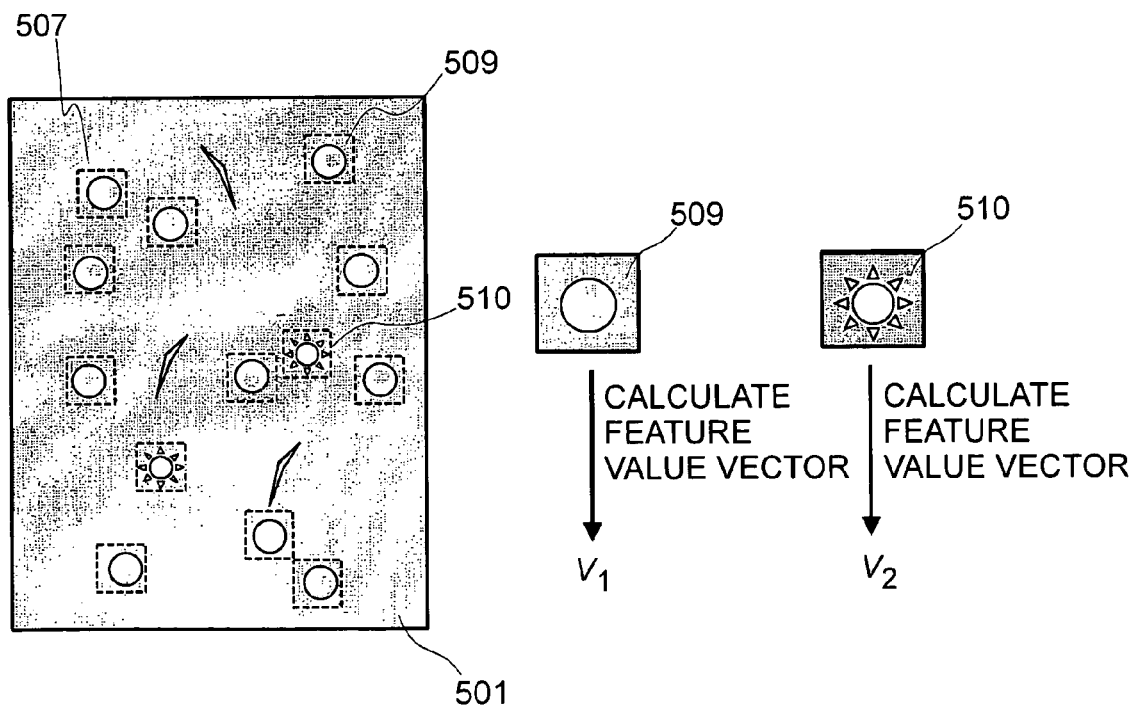
FIG. 5B is a diagram showing the image 501 in which microorganisms 502 and 503, whose feature value vectors are similar to that of a template 506, have been extracted.

The captured image 501 in FIGS. 5A and 5B is relatively large, having side dimensions of 1000 pixels or more, and includes a plurality of microorganism images having dimensions of approximately 128×128 pixels. The template image 506, on the other hand, includes an image of a microorganism (the spherical figure in the template image) also having dimensions of approximately 128×128 Specifically, the captured image 501 shown in FIGS. 5A and 5B includes images of a plurality of microorganisms 503 (hereinafter referred to as viruses A), a plurality of microorganisms 502 (hereinafter referred to as viruses B), and a plurality of foreign objects 504 produced as a result of pretreatment, etc.

The comparison and determination processing begins by locating each microorganism (virus) image within the captured image 501 at step 603. This is accomplished by a template matching technique. This technique compares each portion of the captured image 501 with the template image 506 and calculates the degree of similarity between them; portions having a high degree of similarity to the template image 506 are regarded as microorganism images. The degree of similarity may be represented by the cross-correlation coefficient, etc. The cross-correlation coefficient between two images approaches 1 with increasing similarity between them. Specifically, a local window 505 having a size equal to that of the template image 506 may be defined within the captured image 501 and shifted one pixel at a time. The correlation coefficient between the value of each pixel in this window at each position and that of the corresponding pixel of the template image 506 may be calculated. Then, the correlation coefficient between the image in the local window at each position within the captured image 501 and the template image 506 may be calculated. Of the images defined by the local window 505 at each position, those having a correlation value larger than a predetermined value may be regarded as images of the reference microorganism.

The matching results image 501 schematically shows the results of the above processing; each local area 507 enclosed by a respective dotted line box has been determined to contain a microorganism. Foreign objects 504 having an elongated shape have not been recognized as microorganisms since these images have a low correlation value with the template 506.

It should be noted that in the matching results image 501, each local area 510 containing a microorganism 502 (virus B) has been also determined to contain a microorganism. That is, even though the shape of virus B is slightly different from that of the reference microorganism in the template image 506, their images might be determined to match, since such a difference might not be distinctly reflected in the degree of similarity between them if the degree of similarity is represented by the cross-correlation value between them. The matching results image 501 illustrates such a case. It may be possible to set the cross-correlation threshold value such that each local area 510 containing a microorganism 502 (virus B) is determined to contain no microorganism. However, it is not practical to set such a threshold value. That is, even though the above-mentioned method using cross-correlation coefficients can be used to find portions of the image 501 somewhat similar to the template image 506, it can hardly be used to identify each virus type. To overcome this problem, it is necessary to more accurately calculate the degree of similarity between the template image and each microorganism image within the captured image 501.

One method for accomplishing this is to use a feature value vector of each image. A feature value vector is an array of numerical values obtained as a result of image-processing data indicating features of an imaged microorganism, such as how elongated it is, how jagged its outline is, how bright it is, and whether the texture of its surface is fine or rough.

Step 604 calculates numerical values indicating various features of the reference microorganism in the template 506 through image processing and obtains a feature value vector vd. Then, Step 605 calculates a feature value vector Vn of each microorganism image within the captured image 501 (n denotes a serial number assigned to each microorganism, that is, n=b 1, 2, . . .).

FIGS. 5A and 5B show how to calculate feature value vectors v1 and v2 of the two microorganism images 509 and 510, respectively, within the captured image 501. First, as shown in FIG. 5A, the local window 505 is shifted by one pixel at a time within the captured image 501 to see whether the image in the local window 505 at each position matches the reference microorganism image (the template 506). As a result, the microorganism images 502 and 503 are extracted since they have a feature value vector similar to that of the template 506, as shown in FIG. 5B. Then, the degree of similarity between the template 506 and each microorganism image 502 and 503 is calculated based on the similarity between their feature value vectors. The above-mentioned operation is performed at step 606.

It should be noted that an example of a parameter representing the degree of similarity is the distance between the two feature value vectors, since similar microorganisms have similar vector values (that is, the distance between their vectors is small), and the distance between the vectors of microorganisms of different types is large. Thus, the larger the distance between the feature value vectors of two microorganism images, the lower the degree of similarity between them.

The processing unit 112 calculates the degree of similarity between each microorganism image within the captured image 501 and the template 506, in accordance with the above-mentioned method using feature value vectors, and sends the calculation results to the storage unit 116 before ending the comparison and determination processing. After that, at step 209, the overall control unit reads the results from the storage unit 116 and displays them on the input/output unit 113 so that the operator can view them. The above-described steps are repeated for all reference microorganism images selected by the operator at step 205. Step 206 checks whether all reference microorganism images selected at step 205 have been compared with the captured image.

Thus, in the above-described comparison and determination processing at step 209, the processing unit 112 compares each reference microorganism image with each possible microorganism image within each image of a sample captured after a specific sample pretreatment method for the reference microorganism was applied to the sample, calculates the degree of similarity between them, and then stores each image of the sample, each possible microorganism image, and the degrees of similarity obtained, in the storage unit 116. Then, the overall control unit 115 reads the comparison and determination results from the storage unit 116 and displays them on the input/output unit 113.

Figure 7:
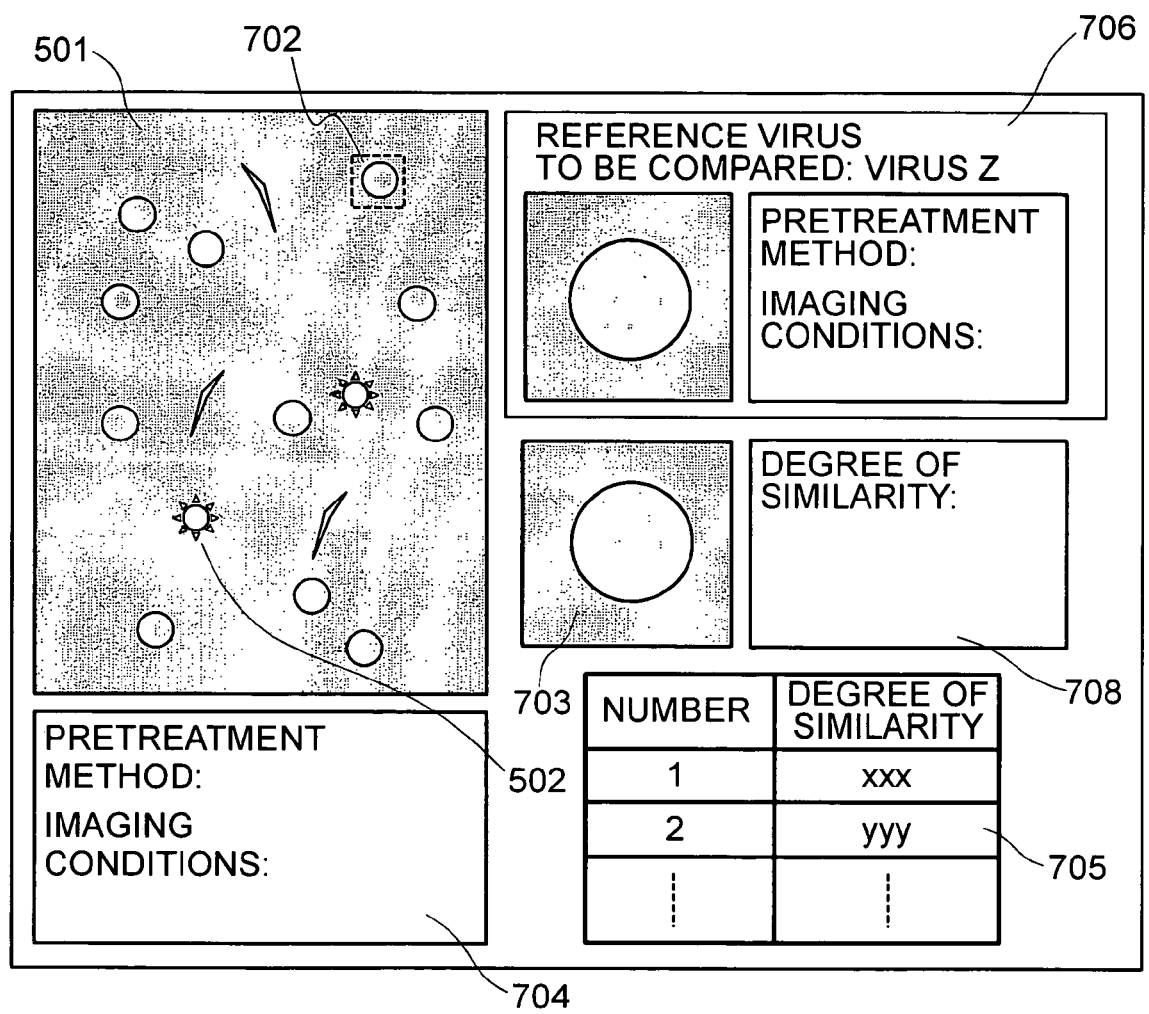
FIG. 7 is a diagram showing an exemplary screen displaying microorganism identification results in the microscope system.

FIG. 7 shows an exemplary screen of the input/output unit 113 displaying the comparison and determination results obtained using the captured image 501. A data window 704 displays the sample pretreatment method and the imaging conditions used when the captured image 501 was obtained so that the operator can easily check them. A current reference image display window 706 displays the current reference image to be compared (obtained from the database) and the sample pretreatment method, the imaging conditions, etc. therefor.

An enlarged image 703 is an image obtained by enlarging a microorganism image (for example, a microorganism image 702 in the figure) arbitrarily selected by the operator from the microorganism images found within the captured image 501. A data window 708 displays the degree of similarity between the enlarged image 703 and the current reference microorganism image.

This arrangement allows the operator to determine how similar the microorganism image arbitrarily selected from the captured image 501 is to the reference microorganism image by observing the images and checking the degree of similarity indicated. Further, a window 705 lists the degree of similarity between each microorganism image found within the captured image 501 and the reference microorganism image.

From the above-described data, the operator can determine the number of microorganism images found within the captured image 501 and easily find microorganisms (for example, microorganisms 502 in FIG. 7) different from the reference microorganisms by checking the degree of similarity of each microorganism image to each reference microorganism image and selecting microorganisms having a low degree of similarity.

Figure 9:
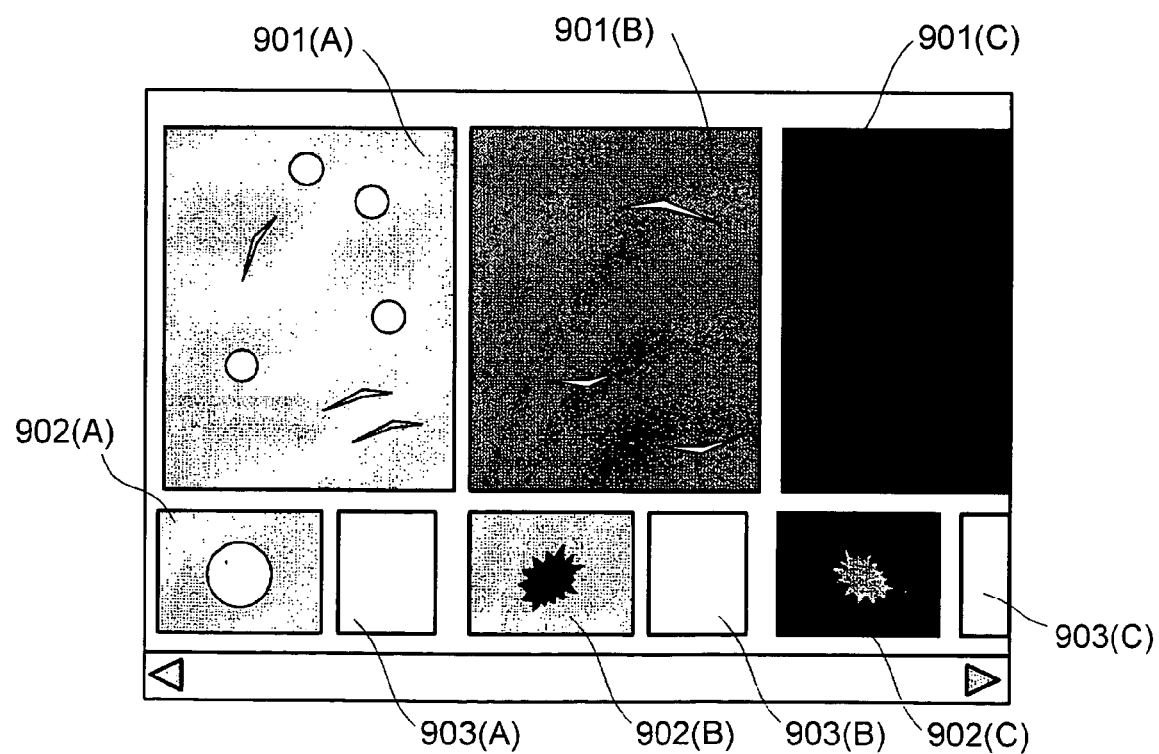
FIG. 9 is a diagram showing an exemplary screen displaying microorganism identification results in the microscope system.

FIG. 9 shows another exemplary screen displaying the comparison and determination results. Specifically, this single screen collectively shows the results of checking whether three reference microorganisms A, B, and C can be found in the same specimen. Reference numerals 901(A), 901(B), and 901(C) denote captured images for the reference microorganisms A, B, and C, respectively; reference numerals 902(A), 902(B), and 902(C) denote the template images of the reference microorganisms A, B, and C, respectively, as retrieved from the database; and reference numerals 903(A), 903(B), and 903(C) denote data windows displaying imaging conditions and sample pretreatment methods for the reference microorganisms A, B, and C, respectively.

In this figure, only the template image of the reference microorganism A matches possible microorganism images within the corresponding captured image. Therefore, it can be determined that the sample contains only the microorganism A; other microorganisms B and C are not in the sample. This screen allows the operator to check a plurality of types of microorganisms contained in a sample at once. Further, on the screen shown in FIG. 9, if the operator has found that the sample contains none of the reference microorganisms, then the operator can take such actions as changing the keywords used for searching the database so as to reevaluate the sample.

Further, this system may be arranged such that after an image of a sample is captured under certain conditions, image data similar to the captured image is retrieved from the database 117 and displayed on the input/output unit 113.

FIG. 4 is a screen shot showing, in list form, image data 403 which was retrieved from the database 117 using the captured microorganism image 401 as a key and, therefore, which is similar to the microorganism image 401, and information 404 on the microorganisms indicated by the image data 403. The image data 403 may be obtained by calculating the degree of similarity between a feature value vector of the captured image and that of each image stored in the database 117 and selecting images having a high degree of similarity to the captured image.

This arrangement allows microorganism images similar to the captured image to be retrieved regardless of the sample pretreatment method and imaging conditions. Then, the pretreatment method and imaging conditions for the current sample under observation may be changed based on the retrieved microorganism images.

Further, the present system may organize the obtained captured images, determination results, and data of each type of microorganism retrieved from the database 117 and display them on the input/output unit 113 such that the operator can easily view them, regardless of whether or not to capture a new image using the imaging system.

According to the present embodiment, as described above, it is possible to efficiently identify microorganisms, etc. contained in an obtained sample by utilizing databases created by research institutes of microorganisms, etc.

It should be noted that the system shown in FIG. 1 uses a transmission electron microscope as a means to capture an image. However, the present invention is not limited to this particular arrangement. Any imaging means can be used to achieve the same function by appropriately controlling the sample pretreatment method and the imaging conditions based on data stored in a database. Further, the database need not necessarily be connected to the imaging system through an internal bus as shown in FIG. 1. The database may be accessed through the input/output 113 having communications means for communicating with an external device.

Figure 8:
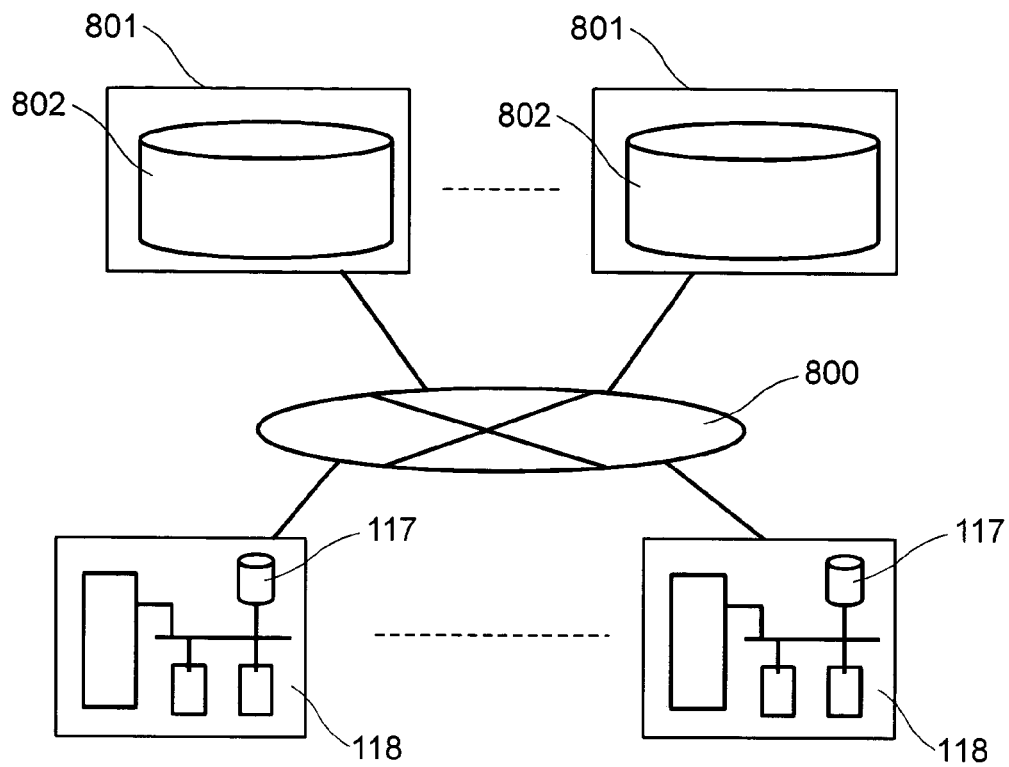
FIG. 8 is a block diagram showing the configuration of a network system according to the present invention.

Another embodiment of the present invention will be described below with reference to FIG. 8. In the figure, one or more transmission electron microscope systems 118 shown in FIG. 1 and one or more database creation sites 801 are connected to a wide area network 800 (e.g., the Internet). Each database creation site 801 has a function to organize and store various types of data of newly-discovered microorganisms, etc. found by research institutes of viruses or microbes as well as newly-acquired information on known microorganisms, etc. in the same form as that of the database shown in FIG. 3 and to publish them on the wide area network 800 as an original database 802.

In this example, a plurality of such database creation sites are connected to the wide area network 800. The present embodiment employs this configuration, since each type of virus and microbe is originally found locally and therefore it is necessary to quickly publish information on newly-discovered viruses, etc. found at a remote location. This arrangement allows each system 118 to update its database 117 with the contents of each original database 802 and thereby perform analysis using the latest data.

To update its local database 117, a system 118 may query each database creation site 801 about the contents of the database 802 of the site at regular intervals and, if the database 802 stores new data, obtain it through the wide area network 800 or another means and store it in the local database 117. Alternatively, the database creation sites 801 may transmit new data to each system 118 when they have stored the data in their original databases 802.

Furthermore, the database creation sites 801 may be configured such that each site can check the data in the original databases of the other sites and gather new data. This arrangement allows a plurality of database creation sites to store the same data in their original databases.

If a plurality of original databases are maintained so as to hold the same data, each system 118 may be able to obtain all currently available data only by accessing a single specific database site. Of course, it would be possible that each system 118 has no local database and directly accesses the original databases through the wide area network 801 to perform comparison and determination processing of a sample.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A transmission electron microscope system comprising:
   database means for storing a plurality of specimen pretreatment methods and a plurality of imaging conditions, each specimen pretreatment method and each imaging condition being for capturing a transmitted electron image of a different type of specimen under a transmission electron microscope, said specimen containing microscopic things such as viruses and proteins;
   selection means, from said plurality of specimen pretreatment methods and said plurality of imaging conditions stored in said database means, for selecting a specimen pretreatment method and an imaging condition suitable for a specimen to be inspected containing microscopic things such as viruses and proteins;
   transmitted electron image capturing means for capturing a transmitted electron image of said specimen to be inspected under said selected imaging condition after said specimen to be inspected is pretreated by said specimen pretreatment method selected by said selection means; and
   image processing means for processing said transmitted electron image captured by said transmitted electron image capturing means to identify said microscopic things present in said specimen to be inspected.

2. The transmission electron microscope system as claimed in claim 1, wherein:
   said database means further stores image information on a plurality of transmitted electron images of different types of specimens; and
   said image processing means processes said transmitted electron image captured by said transmitted electron image capturing means to generate image information and compares said generated image information with said image information stored in said database means to identify said microscopic things present in said specimen to be inspected.

3. The transmission electron microscope system as claimed in claim 1, wherein said database means stores, for each microscopic thing, a name, appearance information, geometrical information such as size and shape, a transmitted electron microscopic image, an acceleration voltage applied when said transmitted electron microscopic image was taken, a specimen pretreatment method used when transmitted electron microscopic image was taken, and information on a human symptom and a human disorder caused by the microscopic thing.

4. The transmission electron microscope system as claimed in claim 1, further comprising:
   input means for inputting a keyword used to retrieve from said database means information on a specimen pretreatment method and an imaging condition for a microscopic thing whose presence or absence in said specimen to be inspected is to be determined; and
   communications means for connecting between said selection means and said input means.

5. The transmission electron microscope system as claimed in claim 4, wherein said image processing means processes said transmitted electron image captured by said transmitted electron image capturing means to extract geometrical information on said specimen to be inspected, such as size and shape.

6. A transmission electron microscope system comprising:
   electron beam irradiation means for emitting an electron beam onto a specimen containing microscopic things such as viruses and proteins;
   transmitted electron image capturing means for focusing electrons transmitted through said specimen to capture a transmitted electron image, said electrons having been emitted by said electron beam irradiation means as said electron beam;
   image processing means for identifying said microscopic things present in said specimen based on said transmitted electron image captured by said transmitted electron image capturing means;
   database means for storing transmitted electron images of different types of microorganisms and, specimen pretreatment methods and imaging conditions for capturing said transmitted electron images by said electron beam irradiation means and said transmitted electron image capturing means, said transmitted electron images having been captured by said transmitted electron image capturing means;
   access means for accessing said database means;
   input means for inputting a keyword for selecting a microscopic thing whose presence or absence in said specimen is to be determined;
   receiving means, based on said keyword input from said input means, for receiving a transmitted electron image of said selected microscopic thing and information on a specimen pretreatment method and an imaging condition from said database means through said access means, said database means storing said transmitted electron image and said information such that said information is associated with said transmitted electron image; and
   display means for displaying said information on said specimen pretreatment method and said imaging condition received by said receiving means.

7. The transmission electron microscope system as claimed in claim 6, further comprising:
   an imaging unit for capturing an image of said specimen under said imaging condition after said specimen is pretreated by said specimen pretreatment method, said specimen pretreatment method and said imaging condition having been received by said receiving means;
   a comparison unit for comparing said image captured by said imaging unit with said image received from said database means; and
   an output unit for outputting a comparison result received from said comparison unit.

8. The transmission electron microscope system as claimed in claim 6, wherein said database means stores, for each microorganism, a name, appearance information, geometrical information such as size and shape, a transmitted electron microscopic image, an acceleration voltage applied when said transmitted electron microscopic image was taken, a specimen pretreatment method used when said transmitted electron microscopic image was taken, and information on a symptom and a disorder caused by the microorganism.

9. The transmission electron microscope system as claimed in claim 6, wherein said keyword for identifying said microscopic thing includes a name of a microorganism, appearance information on said microorganism, geometrical information on said microorganism, such as size and shape, and information on a symptom and a disorder caused by said microorganism, said keyword being input from said input means.

10. The transmission electron microscope system as claimed in claim 7, wherein said output unit displays image data of one or more microorganisms received from said database means, image data obtained from said imaging unit, and comparison results therebetween.

11. An inspection method using a transmission electron microscope system, comprising the steps of:
selecting, from a database, a specimen pretreatment method and an imaging condition suitable for a specimen to be inspected containing microscopic things such as viruses and proteins, said database storing a plurality of specimen pretreatment methods and a plurality of imaging conditions, each specimen pretreatment method and each imaging condition being for capturing a transmitted electron image of a different type of specimen under a transmission electron microscope, said different type of specimen containing microscopic things such as viruses and proteins;
after said specimen to be inspected is pretreated by said selected specimen pretreatment method, capturing a transmitted electron image of said specimen to be inspected under said transmission electron microscope set to said selected imaging condition; and
processing said captured transmitted electron image to identify said microscopic things present in said specimen to be inspected.

12. The inspection method as claimed in claim 11, wherein:
said database further stores image information on a plurality of transmitted electron images of different types of specimens; and
in said step of identifying a microscopic thing, said captured transmitted electron image is processed to generate image information and said generated image information is compared with said image information stored in said database to identify said microscopic thing present in said specimen to be inspected.

13. The inspection method as claimed in claim 11, wherein said database stores, for each microscopic thing, a name, appearance information, geometrical information such as size and shape, a transmitted electron microscopic image, an acceleration voltage applied when said transmitted electron microscopic image was taken, a specimen pretreatment method used when said transmitted electron microscopic image was taken, and information on a human symptom and a human disorder caused by the microscopic thing.

14. The inspection method as claimed in claim 11, further comprising the step of:
inputting, through an input means, a keyword for retrieving from said database information on a specimen pretreatment method and an imaging condition for a microscopic thing whose presence or absence in said specimen to be inspected is to be determined, and allowing said database to be connected through a communications line.

15. The inspection method as claimed in claim 14, wherein said transmitted electron image is processed to extract geometrical information on said specimen to be inspected, such as size and shape.

16. An inspection method using a transmission electron microscope system, comprising the steps of:
emitting an electron beam onto a specimen by electron beam irradiation means, said specimen containing microscopic things such as viruses and proteins;
focusing electrons transmitted through said specimen to capture a transmitted electron image by transmitted electron image capturing means, said electrons having been emitted through said electron beam emission;
storing in a database transmitted electron images of different types of microorganisms and specimen pretreatment methods and imaging conditions for capturing said transmitted electron images by said electron beam irradiation means and said transmitted electron image capturing means;
inputting a keyword for selecting a microscopic thing whose presence or absence in said specimen is to be determined;
retrieving, based on said input keyword, a transmitted electron image of said selected microscopic thing and information on a specimen pretreatment method and an imaging condition from information stored in said database, said information on said specimen pretreatment method and said imaging condition being stored such that said information is associated with said transmitted electron image;
displaying said retrieved information on said specimen pretreatment method and said imaging condition on a screen; and
identifying said microscopic thing present in said specimen based on said captured transmitted electron image.

17. The inspection method as claimed in claim 16, further comprising steps of:
capturing an image of a pretreated specimen;
comparing said captured image with an image received from said database; and
outputting a result of said comparison.

18. The inspection method as claimed in claim 16, wherein said database stores, for each microorganism, a name, appearance information, geometrical information such as size and shape, a transmitted electron microscopic image, an acceleration voltage applied when said transmitted electron microscopic image was taken, a specimen pretreatment method used when said transmitted electron microscopic image was taken, and information on a symptom and a disorder caused by the microorganism.

19. The inspection method as claimed in claim 16, further comprising the step of:
displaying image data of one or more microorganisms received from said database, captured image data, and comparison results therebetween.

* * * * *